(12) United States Patent
Redlingshöfer et al.

(10) Patent No.: US 8,008,530 B2
(45) Date of Patent: Aug. 30, 2011

(54) PROCESS FOR PREPARING METHYL MERCAPTAN

(75) Inventors: Hubert Redlingshöfer, Münchsteinach (DE); Stephan Kretz, Biebergemünd (DE); Caspar-Heinrich Finkeldei, Alzenau (DE); Christoph Weckbecker, Gründau-Lieblos (DE); Wolfgang Böck, Langenselbold (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 469 days.

(21) Appl. No.: 12/065,563

(22) PCT Filed: Aug. 22, 2006

(86) PCT No.: PCT/EP2006/065565
§ 371 (c)(1),
(2), (4) Date: Jul. 28, 2008

(87) PCT Pub. No.: WO2007/028708
PCT Pub. Date: Mar. 15, 2007

(65) Prior Publication Data
US 2009/0054691 A1  Feb. 26, 2009

(30) Foreign Application Priority Data
Sep. 10, 2005 (DE) .......................... 10 2005 043 151

(51) Int. Cl.
*C07C 319/00* (2006.01)

(52) U.S. Cl. ............................................. 568/70; 568/69
(58) Field of Classification Search ........................ None
See application file for complete search history.

(56) References Cited

U.S. PATENT DOCUMENTS

| 2,214,859 | A |   | 9/1940  | Maude et al. |          |
|-----------|---|---|---------|--------------|----------|
| 2,863,725 | A |   | 12/1958 | Maude et al. |          |
| 3,961,035 | A | * | 6/1976  | Mickley      | 423/563  |
| 5,283,369 | A | * | 2/1994  | Clark et al. | 568/71   |
| 5,866,721 | A | * | 2/1999  | Hofen et al. | 568/71   |
| 5,886,230 | A | * | 3/1999  | Hofen et al. | 568/71   |

FOREIGN PATENT DOCUMENTS

| DE | 1768826     | 8/1971  |
| DE | 196 54 515  | 10/1998 |
| FR | 2477538     | 11/1973 |
| GB | 1193040     | 5/1970  |
| WO | WO 01/10776 | 2/2001  |

OTHER PUBLICATIONS

Wiley-VCH, Ullmann's Encyclopedia of Industrial Chemistry, 2002.

* cited by examiner

*Primary Examiner* — Karl J Puttlitz
(74) *Attorney, Agent, or Firm* — Smith, Gambrell & Russell, LLP

(57) ABSTRACT

The present invention relates to a process for continuously preparing methyl mercaptan from hydrogen sulphide and methanol in a direct connection with the preparation of hydrogen sulphide.

16 Claims, No Drawings

PROCESS FOR PREPARING METHYL MERCAPTAN

INTRODUCTION AND BACKGROUND

The present invention relates to a process for continuously preparing methyl mercaptan from hydrogen sulphide and methanol in direct connection with the preparation of hydrogen sulphide.

Methyl mercaptan in particular is an industrially important intermediate, for example for the synthesis of methionine and for the synthesis of dimethyl sulphoxide and dimethyl sulphone. It is currently prepared predominantly from methanol and hydrogen sulphide by reaction over a catalyst composed of aluminium oxide. Methyl mercaptan is commonly synthesized in the gas phase at temperatures between 300 and 500° C. and at pressures between 1 and 50 bar.

In addition to the methyl mercaptan and water formed, the product gas mixture comprises the unconverted methanol and hydrogen sulphide starting materials and dimethyl sulphide and dimethyl ether as by-products, and also small amounts of polysulphides (dimethyl disulphide). Gases inert in the reaction, such as carbon monoxide, carbon dioxide, nitrogen and hydrogen, are also present in the product gas. The methyl mercaptan formed is removed from this reaction mixture. The reactant gas mixture comprises predominantly hydrogen sulphide and methanol in a molar ratio between 1:1 and 10:1.

As explained in DE-1768826, the methyl mercaptan formed is removed from the product gas mixture in several distillation and wash columns at temperatures between 10 and 140° C. The further product streams obtained are excess hydrogen sulphide, methanol, inert gases such as carbon monoxide, carbon dioxide, nitrogen and water. The wash liquid used is preferably methanol. Excess hydrogen sulphide is recycled into the reactor as so-called cycle gas. In addition to hydrogen sulphide, the cycle gas also comprises methanol, methyl mercaptan, dimethyl sulphide and organic components, and consumed hydrogen sulphide and methanol are replaced by supplying fresh media.

The overall process for methyl mercaptan preparation can be divided into two sections. The first section comprises the workup of the reactant gas mixture and its conversion to methyl mercaptan. The second sector includes the separation of the product gas mixture to obtain methyl mercaptan and recycling of the unconsumed feedstocks, and also the disposal of wastewater and offgases.

For economic viability of the process, minimum capital and operating costs are required. Here, the cost for apparatus and machines in particular, but also the energy demand for the synthesis and workup of the reactant gas mixture, constitutes a high cost factor. For example, large electrical outputs are required for the operation of compressors and of heating and cooling circuits.

According to FR 2477538, methyl mercaptan is prepared by compressing fresh hydrogen sulphide gas to 11 bar in a compressor. Thereafter, cycle gas which comprises hydrogen sulphide, dimethyl sulphide, methanol and small amounts of methyl mercaptan and has been recycled from the process is added to the compressed hydrogen sulphide to form the reactant gas mixture. A preheating oven raises the temperature of the gas mixture after the compression to 510° C.

In DE 19654515 too, the compression of the reactant gases to operating pressure is described preferentially in two stages, for example with a two-stage compressor, the gas mixture being compressed in the first stage to an intermediate pressure and in the second stage to the operating pressure. The methanol can be injected directly into the first compressor stage. The reactant gas mixture thus obtained is then heated first to an initial temperature of 150 to 250° C. and then further to the reaction temperature. At this temperature, the reactant gas mixture passes into the reactor for the formation of methyl mercaptan. Owing to the temperature limit in a compression, the temperature after the second compressor stage can be raised to a maximum of 140° C.

This means that the entrance temperature of the hydrogen sulphide before the compression must, for example, be at ambient temperature. Consequently, the hydrogen sulphide prepared beforehand at high temperature must first be cooled and, after the compression, heated again to obtain the reaction temperature for the formation of methyl mercaptan. This cooling and repeated heating requires numerous heat exchangers and high energy costs. Moreover, the hydrogen sulphide for compression should not comprise any impurities or even solids, in order not to damage the compressor.

The synthesis of hydrogen sulphide from the elements hydrogen and sulphur is effected typically by introducing a hydrogen into liquid sulphur and a subsequent reaction chamber in the gas phase. Both catalysed and uncatalysed processes are known.

The industrial production of hydrogen sulphide from the elements proceeds according to Ullmann's Encyclopedia of Industrial Chemistry, Wiley-VCH, 2002, at temperatures of 450° C. and a pressure of 7 bar.

CSSR 190792 describes a process variant for preparing hydrogen sulphide, in which high reaction temperatures are avoided by a comparatively complicated series connection of a plurality of reactors. High temperatures are avoided there especially because of corrosion problems.

GB 1193040 describes the uncatalysed synthesis of hydrogen sulphide at relatively high temperatures of 400 to 600° C. and pressures of 4 to 15 bar. It is stated that the required temperature is determined by the pressure at which the synthesis should proceed. At a pressure of 9 bar, 500° C. are accordingly required.

Overall, there are numerous publications with different catalysts for preparing hydrogen sulphide. For instance, U.S. Pat. No. 2,214,859 describes the use of several different metal oxides and metal sulphides with high conversions of hydrogen. U.S. Pat. No. 2,863,725 describes the use of catalysts such as molybdenum sulphide, cobalt oxide or cobalt molybdate bound to supports such as bauxite or aluminium oxide, in order to prepare substantially sulphur-free hydrogen sulphide.

An important point in the preparation of hydrogen sulphide from sulphur and hydrogen is in particular the temperature control. High temperatures are necessary in order to achieve an equilibrium state in which a molar hydrogen:sulphur ratio in the gas phase of about 1:1 is established. Only this enables the synthesis of pure hydrogen sulphide. With increasing pressure, the temperature has to be increased greatly in accordance with the vapour pressure curve of sulphur, in order to achieve the desired molar ratio of 1:1 in the gas phase. In this context, even small differences in the pressure of, for example, 1 bar or less are of great significance.

It is an object of the invention to provide a novel process for preparing methyl mercaptan.

SUMMARY OF THE INVENTION

The invention provides a process for preparing methyl mercaptan, which is characterized in that the syntheses of hydrogen sulphide and methyl mercaptan are coupled to one another by mixing the reaction mixture which leaves the reactor for hydrogen sulphide synthesis under pressure with methanol and introducing it into the reactor for methyl mercaptan synthesis under pressure, a pressure difference being established between the reactors used for the two syntheses which allows the hydrogen sulphide/methanol mixture (reactant gas) to flow in the direction of the methyl mercaptan reactor.

This pressure difference is generally less than 1 bar, preferably less than 0.6 bar, and is always greater than 0 bar, the higher pressure being in the reactor for the hydrogen sulphide synthesis.

DETAILED DESCRIPTION OF INVENTION

The inventive connection of the reactors for hydrogen sulphide and methyl mercaptan synthesis, in which the reaction mixture leaving the hydrogen sulphide reactor has a pressure higher by from >0 to 1 bar in comparison to the methyl mercaptan reactor, permits the avoidance of the necessary compression of the hydrogen sulphide, as is known from the prior art. In the reactant gas workup, it is also possible in accordance with the invention to dispense with the cooling to ambient temperature and with the reheating. Moreover, small amounts of impurities and residual amounts of sulphur also do not disrupt continuous production, since the fault-prone compressor for this purpose is not required in accordance with the invention. As a result of the higher pressure in the reactant gas workup, the gas density in the apparatus is also increased, which enables a more compact design with constant residence time.

The person skilled in the art is free to select the process steps to be combined to prepare hydrogen sulphide.

In one embodiment for the preparation of hydrogen sulphide, hydrogen is introduced into liquid sulphur at a pressure of 8 to 20 bar and converted in a downstream reaction chamber. The entire arrangement is preferably operated at the same temperature.

Moreover, the conversion to hydrogen sulphide is preferably effected in the presence of a heterogeneous catalyst. The catalyst is a sulphur-resistant hydrogenation catalyst known from the state of art, which preferably consists of a support, for example silicon oxide, aluminium oxide, zirconium oxide or titanium oxide, and one or more of the active elements molybdenum, nickel, tungsten, vanadium, cobalt, sulphur, selenium, phosphorus, arsenic, antimony and bismuth or preferably, their compounds. The catalyst may be used either in the liquid phase or in the gas phase. Depending on the reaction conditions, especially at high temperatures, it is also possible for a portion of the hydrogen sulphide to be formed without the action of a catalyst.

In a further embodiment of the invention, a plurality of, especially two or three, reactors are connected in series. In this case, the hydrogen which has then only been converted partly, together with the hydrogen sulphide formed, is converted in a further reactor for further conversion to hydrogen sulphide, preferably distributed in liquid sulphur and directly in the region of the liquid sulphur, and/or converted further to hydrogen sulphide in a downstream gas chamber. In the case of use of two reactors connected in series, the conversion of hydrogen after the first reactor is generally between 40 and 85%. When three reactors are used, the conversion of hydrogen is 20 to 50% after the first reactor and generally 50 to 85% after the second reactor.

Instead of pure hydrogen, it is also possible to pass contaminated hydrogen through the liquid sulphur. The contaminants may, for example, be carbon dioxide, hydrogen sulphide, water, methanol, methane, ethane, propane, or other volatile hydrocarbons. Preference is given to using hydrogen with a purity greater than 65% by volume, of which preferably more than 98% of the hydrogen used is converted to hydrogen sulphide. The contaminants in the hydrogen or their reaction products are preferably not removed from methyl mercaptan before the synthesis, but rather left in the reactant mixture.

In order to minimize the losses of sulphur, the predominant portion of the sulphur which has not been converted to hydrogen sulphide is removed from the hydrogen sulphide before it is converted to methyl mercaptan and recycled. This is effected, for example, by deposition of sulphur at heat exchanger surfaces, by an adsorption or by an absorption. The temperature should preferably be adjusted such that the sulphur can be removed in liquid form. For this purpose, preference is given to temperatures between 120 and 300° C. Sulphur and/or sulphur compounds are removed at a pressure which is between the pressures established in the synthesis of hydrogen sulphide and methyl mercaptan. Preferably in accordance with the invention, hydrogen sulphide is prepared in the pressure range of >9 to 20 bar and methyl mercaptan in the pressure range of 9 to <20 bar, the pressure in the hydrogen sulphide reactor always assuming the higher value.

Overall, the invention can cut down on numerous apparatuses and machines, some of them very complicated, and also energy costs, which significantly lowers the costs of the synthesis of methyl mercaptan, improves the economic viability and increases the availability of production plants.

EXAMPLE

Hydrogen was introduced continuously at a pressure of 12.2 bar into a reactor which was about half-filled with liquid sulphur, passed into the liquid through a frit (100 μm), and saturated with gaseous sulphur. In the reactor which was heated uniformly at 450° C. was disposed a bed, flowed through by the gas phase, of a commercial hydrogenation catalyst (cobalt oxide and molybdenum oxide, bonded to $Al_2O_3$). The analysis by means of gas chromatography gave a conversion of hydrogen of more than 99%. The gas leaving the reactor was not decompressed and was cooled to approx. 170° C. in a heat exchanger. Liquid sulphur thus removed was fed back into the reactor. The heat content of the hydrogen sulphide obtained at 12.2 bar was utilized to evaporate methanol. The reactant gas mixture which thus comprises hydrogen sulphide and methanol was passed at 340° C. into the reactor operated at 12 bar for conversion to methyl mercaptan. In this reactor, an alkali metal tungstate catalyst according to DE 10338887 was used. Overall, the hydrogen introduced was converted to methyl mercaptan with a constant selectivity of approx. 97%. The continuous process was conducted without disruptions for 500 h.

The invention claimed is:

1. A process for preparing methyl mercaptan, comprising coupling the synthesis of hydrogen sulfide in a first reactor and the synthesis of methyl mercaptan in a second reactor to one another by
    obtaining a hydrogen sulfide mixture comprising uncompressed hydrogen sulfide from the first reactor which has a first pressure and adding methanol to the hydrogen sulfide mixture to give a reaction mixture, and
    introducing the reaction mixture into the second reactor which has a second pressure and preparing methyl mercaptan from said reaction mixture, wherein the first pressure and the second pressure gives a pressure difference which allows the reaction mixture to flow in the direction of the second reactor; and wherein the first pressure being higher than the second pressure.

2. The process according to claim 1, wherein the pressure difference between said first reactor and said second reactor is >0 to <1 bar.

3. The process according to claim 1, wherein the first pressure and the second pressure are more than 8 bar.

4. The process according to claim 1, wherein the first pressure is >9 to 20 bar and the second pressure is 9 to <20 bar.

5. The process according to claim 1, wherein the synthesis of hydrogen sulfide is effected at a temperature between 300 and 500° C.

6. The process according to claim 1, wherein the synthesis of hydrogen sulfide is effected in the presence of a heterogeneous catalyst.

7. The process according to claim 6, wherein the synthesis of hydrogen sulfide is effected in the presence of a heterogeneous hydrogenation catalyst.

8. The process according to claim 6, wherein the synthesis of hydrogen sulfide is effected in the presence of a heterogeneous supported catalyst which comprises one or more active elements selected from the group consisting of molybdenum, nickel, tungsten, vanadium, cobalt, sulfur, selenium, phosphorus, arsenic, antimony, bismuth, silicon, aluminum, titanium, zirconium and compounds thereof.

9. The process according to claim 1, wherein the hydrogen sulfide mixture is prepared in two or more reactors connected in series.

10. The process according to claim 1, wherein hydrogen used to prepare the hydrogen sulfide mixture comprises further substances.

11. The process according to claim 10, wherein hydrogen used has a purity greater than 65% by volume.

12. The process according to claim 1, wherein the hydrogen sulfide mixture comprises by-products or starting materials in addition to uncompressed hydrogen sulfide.

13. The process according to claim 1, wherein sulfur in the hydrogen sulfide mixture is removed before adding methanol to obtain the reaction mixture.

14. The process according to claim 13, wherein the hydrogen sulfide mixture is cooled to not more than 120° C. during or before removal of sulfur and any further sulfur compounds.

15. The process according to claim 13, wherein the hydrogen sulfide mixture, downstream of the first reactor, is cooled at a pressure between 9 and 20 bar and liquid sulfur is removed or recycled.

16. The process according to claim 13, wherein the hydrogen sulfide mixture is purified using adsorbents at a pressure between 9 and 20 bar.

* * * * *